(12) United States Patent
Barbut

(10) Patent No.: US 6,866,647 B2
(45) Date of Patent: Mar. 15, 2005

(54) AORTIC SHUNT WITH SPINAL PERFUSION AND COOLING DEVICE

(75) Inventor: Denise R. Barbut, New York, NY (US)

(73) Assignee: CoAxia, Inc., Maple Grove, MN (US)

(*) Notice: Subject to any disclaimer, the term of this patent is extended or adjusted under 35 U.S.C. 154(b) by 187 days.

(21) Appl. No.: 10/383,482

(22) Filed: Mar. 6, 2003

(65) Prior Publication Data
US 2003/0144624 A1 Jul. 31, 2003

Related U.S. Application Data

(62) Division of application No. 09/440,989, filed on Nov. 16, 1999, now Pat. No. 6,530,894.

(51) Int. Cl.⁷ .................... A61M 5/00; A61M 37/00; A61M 25/00
(52) U.S. Cl. .................... 604/9; 604/6.1; 604/6.13; 604/6.16; 604/284
(58) Field of Search .................... 604/8–10, 28, 604/96.01, 99.04, 101, 104, 174, 264, 247, 256, 284, 4.01, 6.16, 257–258, 523–535, 507–508, 511, 537–539, 164.01–164.1; 128/898; 600/433–435

(56) References Cited
U.S. PATENT DOCUMENTS

| | | |
|---|---|---|
| 4,398,907 A | 8/1983 | Crais |
| 4,586,919 A | 5/1986 | Taheri |
| 4,592,754 A | 6/1986 | Gupte et al. |
| 4,712,551 A | 12/1987 | Rayhanabad |
| 4,979,937 A | 12/1990 | Khorasani |
| 5,453,084 A | 9/1995 | Moses |
| 5,545,135 A | 8/1996 | Iacob et al. |
| 5,746,709 A | 5/1998 | Rom et al. |
| 5,843,050 A | 12/1998 | Jones et al. |
| 5,957,963 A | 9/1999 | Dobak, III |
| 6,139,517 A | 10/2000 | Macoviak et al. |

Primary Examiner—Patricia Bianco
(74) Attorney, Agent, or Firm—O'Melveny & Myers LLP

(57) ABSTRACT

An intravascular device comprising an intra-aortic and extra-aortic component for perfusing the spinal arteries during thoracoabdominal surgeries. The intra-aortic component comprises a catheter having a shunt releasably mounted on a distal end of the catheter. An expandable occluder is disposed about the shunt for occluding the aortic lumen. The extra-aortic component comprises a tubular member having a lumen communicating with a first end and a second end. The first end is adapted for attachment to the shunt. The second end of the second tubular member is attached to a plurality of tubular branches. A cooler may be attached to the second tubular member for providing hypothermic perfusion. When the intra-aortic component is attached to the extra-aortic component, blood flows from the proximal aorta to the spinal arteries through the lumens of the tubular branches. Methods of using the device for spinal perfusion during thoracoabdominal surgeries herein are also disclosed.

18 Claims, 6 Drawing Sheets

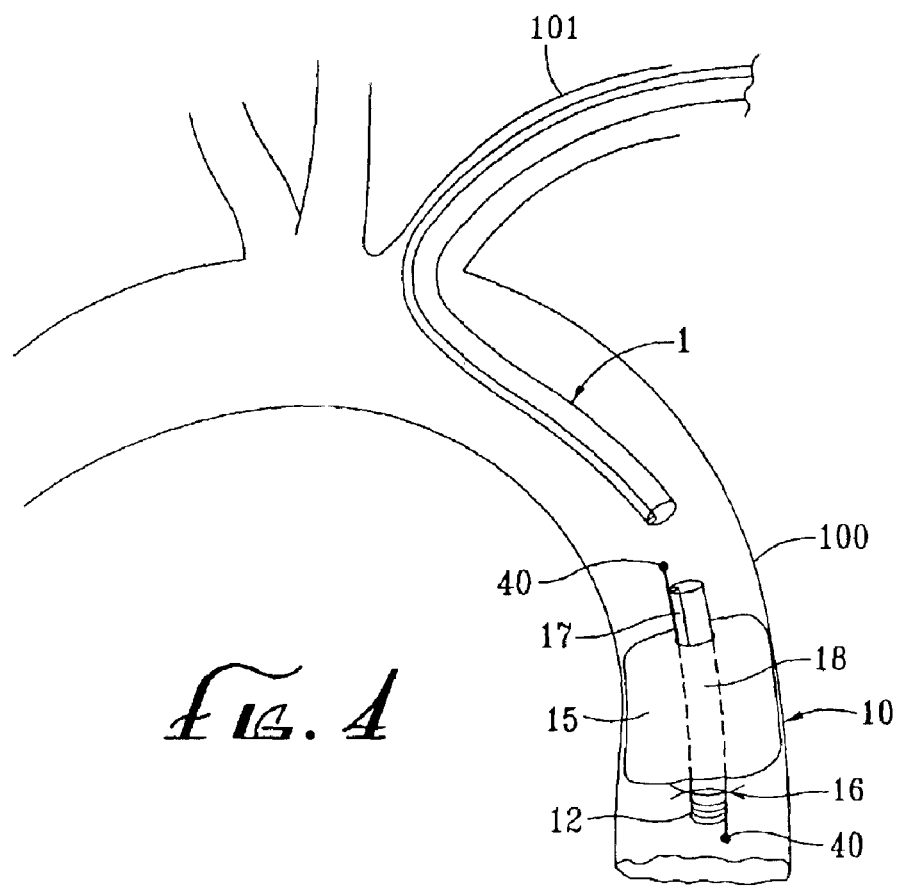

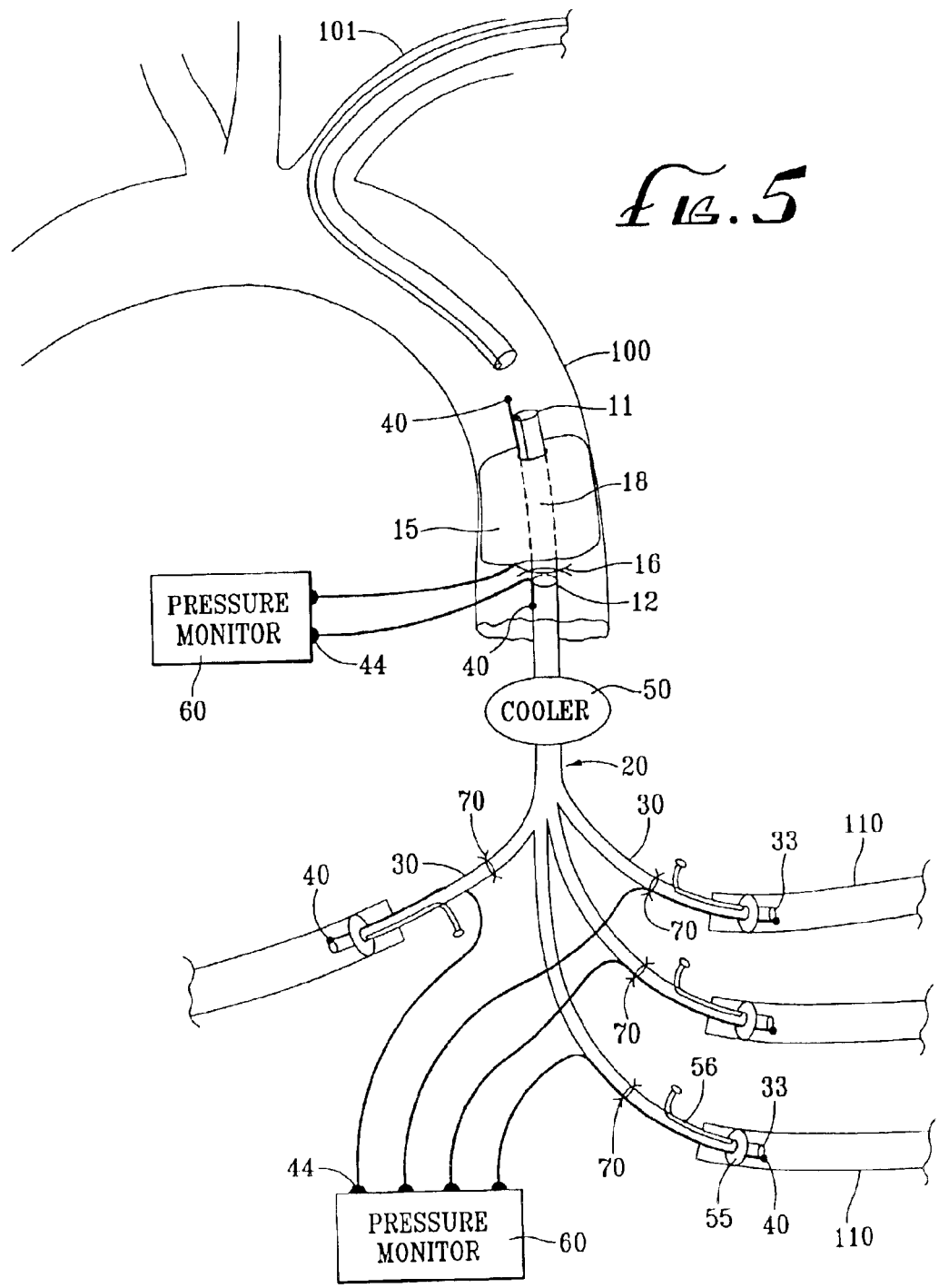

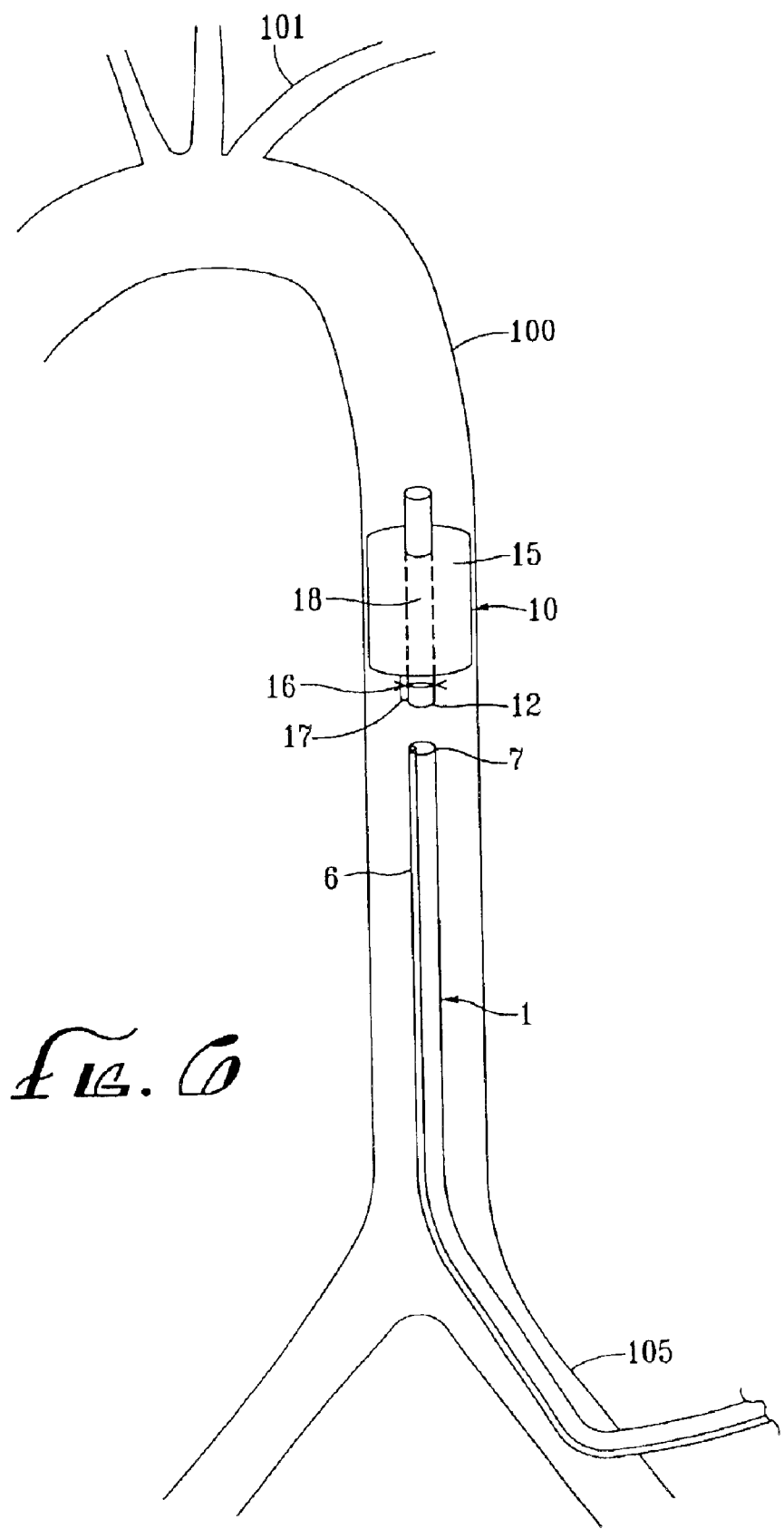

AORTIC SHUNT WITH SPINAL PERFUSION AND COOLING DEVICE

This is a division of U.S. application Ser. No. 09/440,989, filed Nov. 16, 1999, now U.S. Pat. No. 6,530,894, incorporated herein by reference in its entirety.

FIELD OF THE INVENTION

The present invention generally relates to medical devices for perfusing a patient's spinal vasculature during thoracoabdominal surgery. More particularly, the devices comprise an aortic shunt which is releasably mounted to a catheter at a first end of the devices and to a tubular member having tubular branches adapted for insertion into spinal arteries at a second end. The shunt also includes an expandable occluder for occluding the aortic lumen and a valve for controlling fluid or blood flow to the spinal arteries. A cooler may be included for providing hypothermic perfusion to the spinal cord.

BACKGROUND OF THE INVENTION

Thoracoabdominal surgeries, including abdominal aortic aneurysm repair, aortic dissection repair, and aortic thrombectomy, are associated with substantial neurologic morbidity. During abdominal aortic aneurysm repair, for example, an arterial clamp is placed across the aorta for total occlusion and the abdominal aorta is incised or transected for repair. The iliac, the superior mesenteric, and the spinal arteries are often ligated at their origins from the aorta. As a result, spinal cord ischemia can occur in up to 30% of patients. Spinal ischemia is caused partly by lack of blood flow to the spinal cord during aortic clamping, and partly by embolization from the aorta into the spinal arteries.

To reduce the incidence of peri-operative spinal ischemia, several devices were developed to maintain perfusion to the spinal arteries during thoracoabdominal surgeries. Moses describes an internal aortic shunt which perfuses the distal aorta. However, the shunt fails to specifically perfuse the spinal arteries. An intravascular device was described in Rom et al., U.S. Pat. No. 5,746,709, incorporated herein by reference, which involves an intra-aortic pump. Disadvantages associated with this device are that (1) puncturing of the aorta is required for inserting an occluder, (2) arterial clamping is required, which carries the risk of thromboembolism, (3) the aorta needs to be incised for inserting catheters into the spinal arteries.

Rayhanabad developed a single component device for spinal perfusion during aortic surgeries. However, the device cannot be inserted prior to severing of the aorta and therefore failed to eliminate the need for aortic cross clamping and puncture. Khorasani describes an external shunting system with branches to perfuse the spinal arteries through the aorta. However, this system still requires aortic clamping and perforation.

Accordingly, there is a need for devices and methods which provide perfusion to spinal arteries during thoracoabdominal surgeries, and reduce neurologic complication by obviating the need for aortic clamping and puncture.

SUMMARY OF THE INVENTION

The present invention provides intravascular devices which include an intra-aortic and extra-aortic component for perfusing the spinal arteries during thoracoabdominal surgeries. In a first embodiment, the intra-aortic component comprises a catheter having a proximal end, a distal end, and a shunt releasably mounted on the distal end of the catheter. The shunt comprises a tubular member having a lumen communicating with a first end and a second end. An expandable occluder, such as an inflatable balloon, is disposed about the tubular member of the shunt and is adapted to occlude the aortic lumen. The shunt also includes a valve distal to the occluder for controlling blood or fluid flow through the lumen of the shunt.

The extra-aortic component comprises a second tubular member having a lumen communicating with a first end and a second end. The first end is adapted for attachment to the second end of the shunt. In certain embodiments, the second end of the shunt is tapered to facilitate its attachment to the second tubular member. The second end of the second tubular member is attached to a plurality of tubular branches. Each tubular branch has a lumen communicating with the lumen of the second tubular member, and a distal opening adapted to enter a spinal or intercostal artery.

In another embodiment, a manometer is included in the first end and/or second end of the shunt for monitoring pressure upstream or downstream the shunt. In certain embodiments, a manometer is included in the second tubular member or in each tubular branch for monitoring perfusion pressure to the spinal arteries.

In another embodiment, a cooler, or heat exchanger, is attached to the second tubular member for providing hypothermic perfusion to the spinal cord. Perfusing the spinal cord at below the normal body temperature, typically at 34° C., is known to protect the spinal cord from ischemic insult. In certain embodiments, an expandable occluder is mounted on a distal region of each tubular member for preventing back leak of blood during perfusion of the spinal arteries. A valve may be included in the distal region of the tubular branch for controlling blood flow through the spinal artery.

Using the devices described above for perfusing the spinal vasculature during thoracoabdominal surgeries, the catheter, having the shunt attached at its distal end, is inserted into the aorta through a peripheral artery, such as the subclavian or the femoral artery. Prior to insertion, the occluder is placed in a collapsed state, and the valve is turned off to allow no flow through the lumen of the shunt. After the shunt is positioned proximal, i.e., upstream, to the region of interest in the aorta, the occluder is expanded to occlude the aortic lumen, thereby obviating the need for aortic cross clamping. The shunt is then released from the catheter. Incision(s) downstream of the occluder are made for aortic repair. The first end of the second tubular member is attached to the second end of the shunt. The distal end of each tubular branch is inserted into the spinal arteries, and sealed from back leakage of blood. The valve on the shunt is then opened to allow blood flow through each tubular branch to perfuse the spinal vasculature.

In another method, prior to perfusing the spinal arteries, the blood is cooled to below body temperature by a cooler attached to the second tubular member. The tubular branches can also be inserted into the iliac, the mesenteric, or the renal arteries to perfuse the bowel or the kidney in addition to perfusing the spinal cord. Pressures in the proximal aorta and the tubular branches can be measured by manometers included in the shunt and/or the tubular branches. The valves in the shunt and/or the tubular branches can be partially opened or closed to maintain adequate perfusion to the spinal vasculature.

It will be understood that there are several advantages in using the intravascular devices and methods disclosed herein for spinal perfusion during thoracoabdominal surgeries. For example, the devices (1) provide perfusion to the spinal arteries throughout the entire vascular procedure, (2) provide hypothermic perfusion to the spinal cord, (3) reduce the risk of embolization by obviating the need for aortic corssclamping prior to severing the aorta, (4) can be used to perfuse renal and/or mesenteric arteries, (5) do not require a pump, and (6) do not require systemic heparinization, thereby avoiding the risk of systemic hemorrhage.

BRIEF DESCRIPTION OF THE DRAWINGS

FIG. 4 depicts the device of FIG. 3 inserted into the aorta through the left subclavian artery.

FIG. 5 depicts the device of FIG. 3 inserted into the aorta and perfusing the spinal arteries.

FIG. 6 depicts an embodiment of the intravascular device inserted into the descending aorta through the left femoral artery.

DETAILED DESCRIPTION

Figure 1:
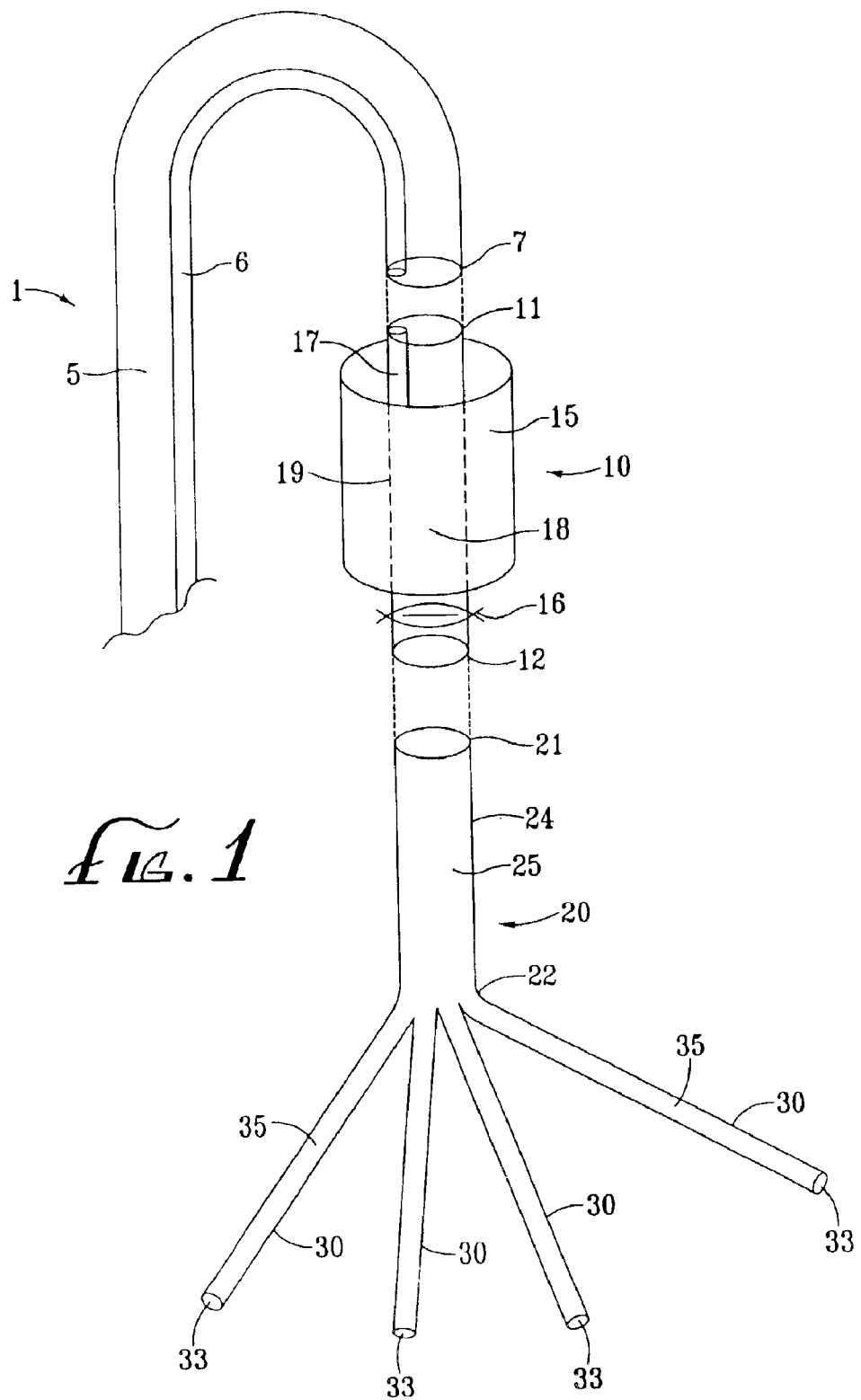
FIG. 1 depicts an embodiment of the intravascular device for perfusing the spinal vasculature during thoracoabdominal surgery according to the present invention.

Referring now to the drawings, an embodiment of the intravascular device for perfusing a patient's spinal vasculature during thoracoabdominal surgery is depicted in FIG. 1. The device generally comprises an intra-aortic component having catheter 1 and aortic shunt 10, and an extra-aortic component 20. Catheter 1 has lumen 5 communicating with a proximal end and distal end 7. Aortic shunt 10 comprises tubular member 19 which has lumen 18 communicating with proximal end 11 and distal end 12. First end 11 of the shunt is releasably mounted to distal end 7 of the catheter. Expandable occluder 15, shown here as an inflatable cylindrical balloon, is disposed about tubular member 19, and communicates with inflation lumen 17. When shunt 10 is mounted to catheter 1, inflation lumen 17 communicates with inflation lumen 6 of the catheter. Shunt 10 also includes valve 16 distal to occluder 15 for controlling fluid or blood flow through lumen 18 of the shunt.

Second component 20 comprises second tubular member 24 having lumen 25 which communicates with first end 21 and second end 22. First end 21 can be attached to second end 12 of the shunt. Second end 22 communicates with 2, 3, 4, 5, 6, 7, 8, or any other number of tubular branches adapted for insertion into the spinal arteries. In FIG. 1, second end 22 is attached to four tubular branches 30, each having lumen 35 and distal opening 33. When second tubular member 24 is attached to shunt 10, lumens 35 of the tubular branches communicate with lumen 18 of the shunt to allow blood or fluid flow from the shunt to distal openings 33.

Figure 2:
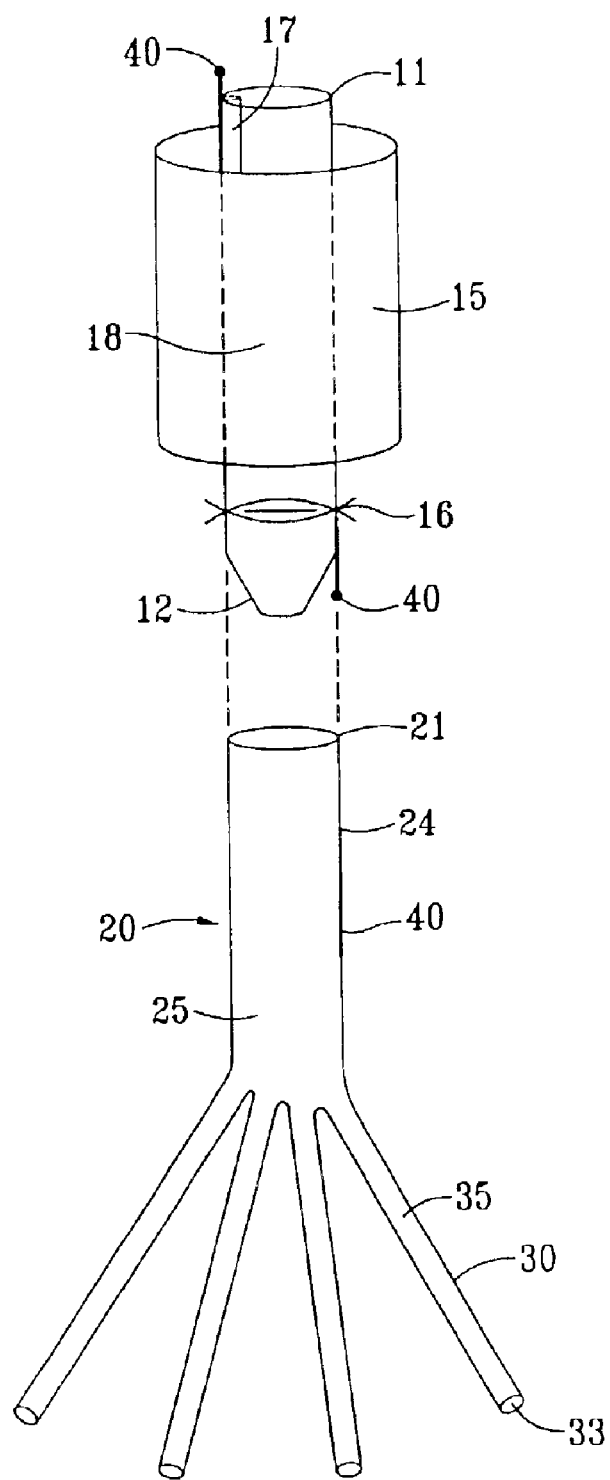
FIG. 2 depicts another embodiment of the intravascular device having manometers for measuring aortic pressure and perfusion pressure to the spinal arteries.

In certain embodiments, distal end 12 of the shunt is tapered as shown in FIG. 2 to facilitate attachment of extra-aortic component 20 to the shunt. Manometers 40 are included in one or both of first end 11 and second end 12 of the shunt for measuring, respectively, pressures proximal and distal the shunt. Manometer 40 is also included in second tubular member 24 for measuring perfusion pressure through lumen 25.

Figure 3:
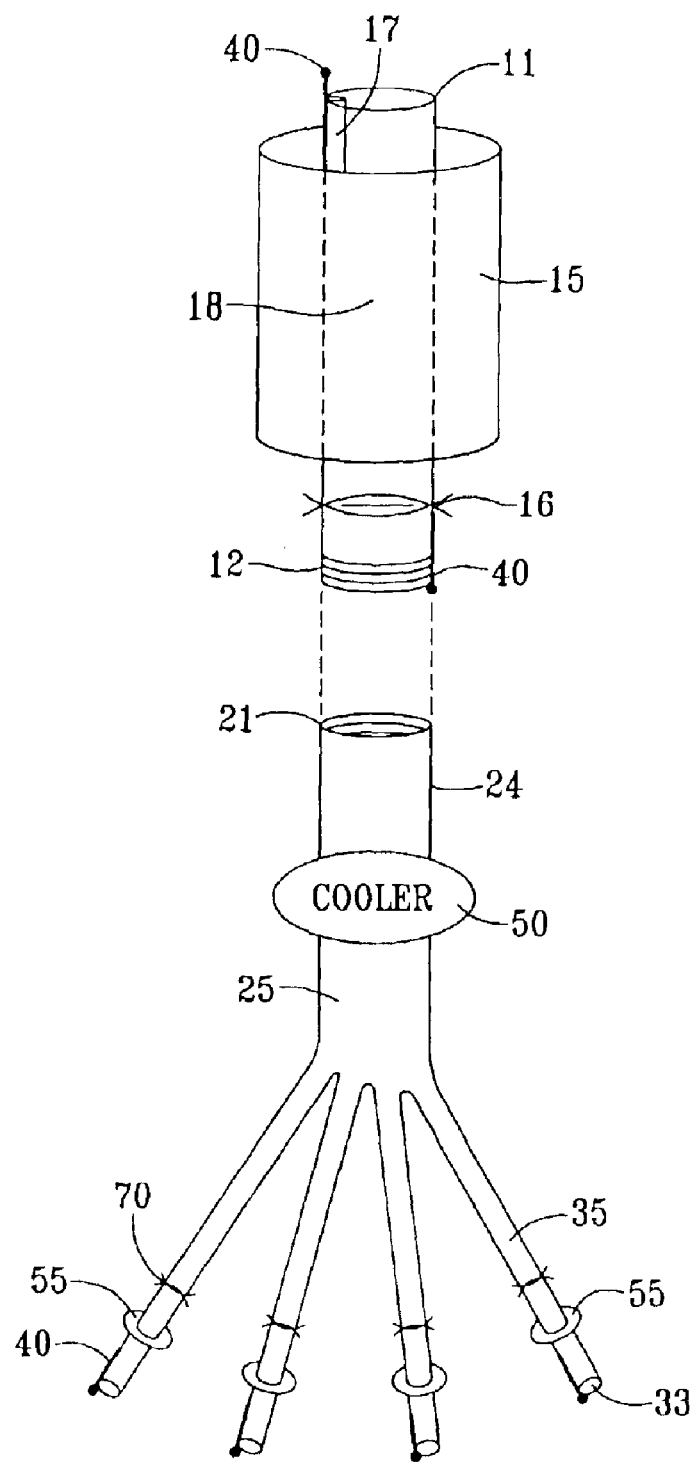
FIG. 3 depicts another embodiment of the intravascular device having a cooler for providing hypothermic perfusion to the spinal vasculature.

FIG. 3 depicts another embodiment of the device having cooler 50 attached to second tubular member 24 for providing hypothermic perfusion to the spinal vasculature. Distal end 12 of the shunt and proximal end 21 of the second tubular member include threads 66 which mate. The second tubular member is thus attached to the shunt by a screwing mechanism. Expandable occluders 55 are disposed about a distal region of each tubular branch for providing a seal in the spinal artery to prevent back leakage of blood during spinal perfusion. Each tubular branch also includes valve 70 for controlling blood flow through the spinal artery, and manometer 40 which measures the perfusion pressure in each spinal artery.

In use, the intra-aortic component of the device is inserted into the aorta through an incision on a peripheral artery during or prior to surgery. In FIG. 4, catheter 1 and shunt 10 are inserted through left subclavian artery 101 into the descending aorta 100, thereby avoiding dissection which might occur when going through an aneurysm. Prior to insertion, shunt 10 is mounted on distal end 7 of the catheter with occluder 15 in a collapsed state and valve 16 in a closed position to facilitate entry into the vessel. Occluder 15 is expanded by infusing fluid or air through inflation lumen 17. After shunt 10 is secured in the aorta proximal the region of interest, the shunt is released from catheter 1. The expanded occluder, by occluding the aortic lumen, eliminates the need for aortic cross clamping. An incision can then be made downstream of the occluder for repair of the diseased aorta.

After the aorta is opened, extra-aortic component 20 is attached to the tubular member of the shunt as shown in FIG. 5. Having occluders 55 in a deflated state and valves 70 in a closed position, the distal end of each tubular branch 30 is inserted into a spinal artery 110. Alternatively, the tubular branch may be inserted into the iliac, mesenteric, and/or the renal artery to perfuse the bowel and the kidney. After insertion into the spinal artery, occluder 55 on tubular member 30 is inflated by infusing fluid or air into inflation lumen 56 which communicates with the occluder. In this way, the distal end of each tubular member is sealed by the occluder to prevent back leakage of blood. Valves 16 and 70 are then opened to allow blood flow from the proximal aorta into the spinal arteries through tubular branches 30. The above sequence of inserting the tubular branch and opening valve 70 can be repeated for each subsequent spinal artery. The blood may be cooled by cooler 50 before entering tubular branches 30 to provide hypothermic perfusion to the spinal vasculature. The pressure in the proximal aorta and the shunt can be measured by manometer 40 mounted on first end 11 and second end 12 of the shunt. The perfusion pressure in each spinal artery can be measured by manometers 40 mounted on the distal region of each tubular branch 30. The manometers are connected to pressure monitor 60 at their proximal end 44. According to the pressure readings displayed on the pressure monitor, the pressure to the spinal arteries can be controlled by partially opening or closing valve 16 and valves 70 to ensure adequate perfusion.

In less risky patients, e.g., patients with less complicated and/or less advanced lesions, the device can be inserted into the aorta through the femoral artery. In FIG. 6, catheter 1 and shunt 10 are inserted through an incision on left femoral artery 105. Prior to insertion, shunt 10 is attached to catheter 1 at second end 12. Inflation lumen 17, which communicates with occluder 15, is included in the second end of the shunt. When the shunt is attached to catheter 1, lumen 17 communicates with lumen 6 in the catheter for inflating occluder 15. After shunt 10 is secured in the aorta upstream of the region of interest, the shunt is released from catheter 1, and the surgeon can then proceed with aortic repair.

The length of the catheter will generally be between 40 and 120 centimeters, preferably approximately between 60 to 80 centimeters. The length of the shunt will generally be between 5 and 20 centimeters, preferably approximately between 10 to 15 centimeters. The inner diameter of the shunt will generally be between 0.5 and 2.5 centimeters, preferably approximately 1 and 2 centimeters. The length of each tubular branch will generally be between 5 and 20 centimeters, preferably approximately 10 and 15 centimeters. The diameter of the expanded occluder on the shunt will generally be between 2 and 6 centimeters, preferably approximately 3 and 5 centimeters. The diameter of the expanded occluder on the tubular branches will generally be between 0.2 and 2 centimeters, preferably approximately 0.5 and 1 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claim. It will also be understood that each feature of each embodiment discussed herein and of each reference cited herein, can be used in any other embodiment.

What is claimed is:

1. A method for perfusing the spinal vasculature of a patient, comprising the steps of:

inserting a catheter into the aorta, the catheter having a proximal end, a distal end, and a shunt releasably mounted on the distal end, the shunt comprising a tubular member having a first end, a second end, and a lumen therebetween, an expandable occluder disposed about the tubular member, and a valve to control fluid flow through the lumen;

expanding the occluder;

releasing the shunt by detaching the shunt from the catheter;

making an incision in the aorta downstream of the occluder, attaching a first end of a second tubular member to the tubular member of the shunt, the second tubular member having a second end, a lumen, and a plurality of tubular branches attached to the second end of the tubular member, each tubular branch having a lumen communicating with the lumen of the tubular member;

inserting the distal end of each tubular branch into a spinal artery;

sealing the distal end of each tubular branch; and opening the valve to flow blood through each tubular branch into the spinal arteries.

2. The method of claim 1, further comprising the step of inserting the catheter through an incision on a peripheral artery.

3. The method of claim 2, wherein the artery is the right subclavian artery.

4. The method of claim 2, wherein the artery is the left subclavian artery.

5. The method of claim 2, wherein the artery is the femoral artery.

6. The method of claim 1, further comprising a cooler attached to the second tubular member.

7. The method of claim 1, further comprising the step of cooling the blood before perfusing the arteries.

8. The method of claim 1, wherein the first end of the second tubular member is attached to the tubular member of the shunt by matching threads.

9. The method of claim 1, wherein the shunt includes a manometer.

10. The method of claim 1, further comprising the step of measuring aortic pressure.

11. The method of claim 1, wherein the second tubular member includes a manometer.

12. The method of claim 1, further comprising the step of measuring perfusion pressure to the arteries.

13. The method of claim 1, wherein the artery is the spinal artery.

14. The method of claim 1, wherein the artery is the intercostal artery.

15. The method of claim 1, wherein the artery is the renal artery.

16. The method of claim 1, wherein the artery is the superior mesenteric artery.

17. The method of claim 1, wherein the artery is any artery originating directly from the aorta.

18. The method of claim 1, wherein the step of making an incision in the aorta comprises severing the aorta.

* * * * *